United States Patent
Everett et al.

(10) Patent No.: US 10,610,552 B2
(45) Date of Patent: *Apr. 7, 2020

(54) NUTRIENT RICH GERMINANT COMPOSITION AND SPORE INCUBATION METHOD

(71) Applicant: NCH Corporation, Irving, TX (US)

(72) Inventors: Gabriel F. K. Everett, Coppell, TX (US); Charles Greenwald, Dallas, TX (US); Judy Pruitt, Mesquite, TX (US); Amanda Rosmarin, Lewisville, TX (US); Jordan Church, Lewisville, TX (US); Daniel Aberle, Irving, TX (US); George Aboagye, Derby (GB)

(73) Assignee: NCH Corporation, Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/479,773

(22) Filed: Apr. 5, 2017

(65) Prior Publication Data

US 2017/0281696 A1 Oct. 5, 2017

Related U.S. Application Data

(60) Provisional application No. 62/318,587, filed on Apr. 5, 2016.

(51) Int. Cl.
| | |
|---|---|
| *A61K 35/742* | (2015.01) |
| *A23L 29/00* | (2016.01) |
| *A61K 47/02* | (2006.01) |
| *C02F 3/34* | (2006.01) |
| *C12N 1/04* | (2006.01) |
| *C12N 1/20* | (2006.01) |
| *C12N 3/00* | (2006.01) |
| *C12R 1/01* | (2006.01) |
| *C12R 1/07* | (2006.01) |
| *C12R 1/125* | (2006.01) |

(52) U.S. Cl.
CPC .......... *A61K 35/742* (2013.01); *A23L 29/065* (2016.08); *A61K 47/02* (2013.01); *C02F 3/34* (2013.01); *C02F 3/348* (2013.01); *C12N 1/04* (2013.01); *C12N 1/20* (2013.01); *C12N 3/00* (2013.01); *C12R 1/01* (2013.01); *C12R 1/07* (2013.01); *C12R 1/125* (2013.01)

(58) Field of Classification Search
None
See application file for complete search history.

(56) References Cited

U.S. PATENT DOCUMENTS

| | | | |
|---|---|---|---|
| 6,327,965 B1 | 12/2001 | Tien | |
| 7,081,361 B2 | 7/2006 | Pearce, III et al. | |
| 9,011,834 B1 | 4/2015 | McKenzie et al. | |
| 9,447,376 B2 | 9/2016 | Hashman et al. | |
| 9,932,543 B2 | 4/2018 | Hashman et al. | |
| 2003/0228679 A1* | 12/2003 | Smith | A01N 63/00 435/235.1 |
| 2008/0241226 A1 | 10/2008 | Abeln et al. | |
| 2009/0186057 A1 | 7/2009 | Farmer et al. | |
| 2009/0232941 A1 | 9/2009 | Farmer | |
| 2014/0295482 A1 | 10/2014 | Lyte | |
| 2016/0362654 A1 | 12/2016 | Hashman et al. | |

FOREIGN PATENT DOCUMENTS

| | | | | |
|---|---|---|---|---|
| WO | WO199905310 | | 2/1999 | |
| WO | WO-2004024865 A2 | * | 3/2004 | ............. A01N 63/00 |
| WO | WO-2014193746 A1 | * | 12/2014 | ............. A01N 63/00 |
| WO | WO2016044661 | | 3/2016 | |

OTHER PUBLICATIONS

Gurung et al. BioMed Research International, vol. 2013, article ID 329121, 18 pages.*
Yazdi et al. Journal of General Microbiology (1990), 136, 1335-1342.*
Busta, F.F. and Ordal, Z.J., Use of Calcium Dipicolinate for Enumeration of Total Viable Endospore Populations without Heat Activation, Applied Microbiology, Mar. 1964, p. 106-110, vol. 12, No. 2, American Society for Microbiology.

(Continued)

*Primary Examiner* — Oluwatosin A Ogunbiyi
(74) *Attorney, Agent, or Firm* — Ross Barnes LLP; Robin L. Barnes

(57) ABSTRACT

A nutrient-germinant composition to aid in spore germination and a method for increased spore germination efficiency. The composition comprises L-amino acids, D-glucose and/or D-fructose, a phosphate buffer, an industrial preservative, and may include bacteria spores or they may be separately combined for germination. The method comprises providing a nutrient-germinant composition and bacteria spores, preferably of one or more *Bacillus* species, and heating to a preferred elevated temperature range of 41° C. to 44° C. for an incubation period of around 2 to 60 minutes. The nutrient-germinant composition is preferably in a concentrated liquid form that is diluted just prior to initiating the germination/incubation method at the point of use. The method may also include dispensing a germinated spore solution to a point-of-use/consumption, such as animal feed, water, or bedding, or a wastewater system or drain.

63 Claims, 3 Drawing Sheets

(56) References Cited

OTHER PUBLICATIONS

Carrillo-Martinez, Yarery and Setlow, Peter, Properties of Bacillus subtilis Small, Acid-Soluble Spore Proteins with Changes in the Sequence Recognized by Their Specific Protease, Journal of Bacteriology, Sep. 1994, p. 5357-5363, vol. 176, No. 17, American Society for Microbiology.
Kleijn, Roelco; Buescher, Joerg M.; Le Chat, Ludovic; Jules, Matthieu; Aymerich, Stephane; and Sauer, Uwe, Metabolic Fluxes during Strong Carbon Catabolite Repression by Malate in Bacillus subtilis, Journal of Biological Chemistry, Jan. 15, 2010, p. 1587-1596, vol. 285, No. 3, The American Society for Biochemistry and Molecular Biology, Inc.
Kong, Lingbo; Zhang, Pengfei; Wang, Guiwen; Yu, Jing; Setlow, Peter; and Li, Yong-Qing, Charactization of bacterial spore germination using phase-contrast and fluorescence microscopy, Raman spectroscopy and optical tweezers, Nature Protocols, Mar. 2011, p. 625-639, vol. 6, No. 5.
Madslien, Elisabeth H.; Granum, Per Einar; Blatny, Janet M; and Lindback, Toril, L-alanine-induced germination in Bacillus licheniformis—the impact of native gerA sequences, BMC Microbiology, published 2014, p. 1-10.
Martin, J. H. and Harper, W. J., Germination Response of Bacillus Licheniformis Spores to Amino Acids, Department of Dairy Technology, Journal of Dairy Science, Jul. 1963, p. 663-667.
Segev, Einat; Rosenberg, Alex; Mamou, Gideon; Sinai, Lior; and Ben-Yehuda, Sigal, Molecular Kinetics of Reviving Bacterial Spores, Journal of Bacteriology, May 2013, p. 1875-1882, vol. 195, No. 9.
Setlow, Peter, Summer Meeting 2013—when the sleepers wake: the germination of spores of *Bacillus* species, Journal of Applied Microbiology, Sep. 2013, p. 1251-1268.
Sinai, Lior; Rosenberg, Alex; Smith, Yoav; Segev, Einat; and Ben-Yehuda, Sigal, The Molecular Timeline of a Reviving Bacterial Spore, Molecular Cell, Feb. 2015, p. 695-707.
Yi, Xuan and Setlow, Peter, Studies of the Commitment Step in the Germination of Spores of *Bacillus* Species, Journal of Bacteriology, Jul. 2010, p. 3424-3433, vol. 192, No. 13.
Zhang, Pengfei; Setlow, Peter; and Li, Yongqing, Characterization of single heat-activated Bacillus spores using laser tweezers Raman spectroscopy, Optics Express, Sep. 2009, p. 16480-16491, vol. 17, No. 19.
Curran et al., Heat Activation Inducing Germination in the Spores of Thermotolerant and Thermophilic Aerobic Bacteria, Journal of Bacteriology; Apr. 1945; vol. 49, No. 4, pp. 335-346.
sigmaaldrich.com, Buffer Reference Center, Webpage [online]; Apr. 30, 2015 [date verified by web.archive.org; retrieved on Jun. 2, 2017]. Retrieved from the Internet: URL: www.sigmaaldrich.com/life-science/core-bioreagents/biological-buffers/learning-center/buffer-reference-center.
Stewart et al., Commitment of bacterial spores to germinate: A measure of the trigger reaction. Biochemical Journal. Jul. 15, 1981, vol. 198, No. 1; pp. 101-106.
Boukarim et al., Preservatives in Liquid Pharmaceutical Preparations; The Journal of Applied Research; published 2009 (month unknown); vol. 9, No. 1-2; pp. 14-17.
Nagler, et al., High Salinity Alters the Germination Behavior of Bacillus subtilis Spores with Nutrient and Nonnutrient Germinants. Applied and Environmental Microbiology. Feb. 2014, vol. 80, No. 4; pp. 1314-1321.
Yasuda, Yoko and Tochikubo, Kunio, Relation between D-Glucose and L- and D-Alanine in the Initiation of Germination of Bacillus subtilis Spore, Microbio. Immunol. Oct. 1983, p. 197-207, vol. 28. No. 2.
Cutting, Simon M., Bacillus Probiotics, Food Microbiology, 2011, vol. 28, pp. 214-220.
Aquadhi Chedia et al, Optimization of nutrient-induced germination of Bacillus sporothermodurans spores using response surface methodology, Food Microbiology, Academic Press Ltd, V. 36, N. 2, Jul. 8, 2013, pp. 320-326.
Ramirez-Peralta Arturo et al, Effects of 1-16 sporulation conditions on the germination and germination protein levels of Bacillus subtilis spores, Applied and Environmental Microbiology Apr. 2012, V. 78, N. 8 Apr. 2012, pp. 2689-2697.
Wang Shiwei et al, Slow Leakage of Ca-Dipicolinic Acid from Individual Bacillus Spores during Initiation of Spore Germination, Journal of Bacteriology, V. 197, N. 6, Mar. 2015, pp. 1095-1103.
Stephanie Luu et al, The Effects of Heat 1-16 Activation on Bacillus Spore Germination, with Nutrients or under High Pressure, with or without Various Germination Proteins, Applied and Environmental Microbiology, V. 81, N. 8, Feb. 13, 2015, pp. 2927-2398.

\* cited by examiner

NUTRIENT RICH GERMINANT COMPOSITION AND SPORE INCUBATION METHOD

CROSS REFERENCE TO RELATED APPLICATION

This application claims the benefit of U.S. provisional patent application No. 62/318,587 filed Apr. 5, 2016.

BACKGROUND OF THE INVENTION

1. Field of the Invention

The present invention relates to a nutrient-germinant concentrate composition and a point-of-use incubation method of germinating bacterial spores.

2. Description of Related Art

Spore germination is a multistep, causative process wherein spores effectively wake-up or are revived from a dormant state to a vegetative growth state. The first step is one by which spores are activated and are induced to germinate, typically by an environmental signal called a germinant. This signal can be a nutrient such as an L-amino acid. Nutrient germinants bind to receptors in the inner-membrane of the spore to initiate germination. Additionally, sugars have been shown to increase the binding affinity of L-amino acids for their cognate receptors.

The germinant signal then initiates a cascade that causes the release of Dipicolinic Acid (DPA), which is stored in a 1:1 ratio with $Ca^{2+}$ (CaDPA) in the core of the spore. The release of CaDPA is a fast process and is typically >90% complete in 2 min. CaDPA release represents a point of no return for spores in which they are committed to the germination process. Those knowledgeable in the art refer to this step as the "commitment" step.

After CaDPA release, the spore is partially hydrated and the core pH rises to approx. 8.0. The core of the spore then expands and the cortex (composed mostly of peptidoglycan) is degraded by core lytic enzymes. The spore absorbs water and consequently loses its refractivity. This loss of refractivity towards the end of the germination process allows spore germination to be monitored via phase-contrast microscopy.

The second phase of germination is an outgrowth step in which the spore's metabolic, biosynthetic, and DNA replication/repair pathways initiate. The outgrowth period has several phases. The first is known as a ripening period in which no morphological changes (such as cell growth) occur, but the spore's molecular machinery (e.g. transcription factors, translation machinery, biosynthesis machinery, etc.) is activated. This period can vary in length based on the initial resources that are packaged with the spore during the process of sporulation. For instance, the preferred carbon source of several *Bacillus* species (including *subtilis*) is malate and *Bacillus* spores typically contain a large pool of malate that is used during the revival process. Interestingly, deletion mutants that cannot utilize the malate pool display an extended ripening period compared to wild-type spores indicating that the spore malate pool is sufficient to energize the initial outgrowth process. Additionally, spores store small, acid-soluble proteins that are degraded within the first several minutes of revival that serve as an immediate source of amino acids for protein synthesis. After the outgrowth step, spore revival is complete and cells are considered to be vegetatively growing.

It is known that spores can be induced to germinate via heat-activation. Spores of various *Bacillus* species have been heat-activated at strain-specific temperatures. For example, *B. subtilis* spores have been heat-activated at 75° C. for 30 minutes while *B. licheniformis* spores have been heat-activated at 65° C. for 20 minutes. The heat-activation has been shown to cause a transient, reversible unfolding of spore coat proteins. Heat-activated spores can then be germinated for additional time in germination buffers containing nutrient germinants, such as L-alanine. If no nutrient germinant is present, however, spores will return to their pre-heated, non-germinated state.

It is also known that germination can occur at ambient temperatures (near typical room temperature) without heat-activation and with a germination buffer containing nutrients, but the process usually takes longer than with heat-activation. For example, *B. licheniformis* and *B. subtilis* spores will germinate at 35° C. or 37° C., respectively, but it takes a longer period of time (e.g. 2 hours) in a germination buffer containing nutrient germinants. Additionally, non-heat-activated spores of *B. subtilis* have been known to have been germinated in non-nutrient germinant conditions (e.g. $CaCl_2+Na_2DPA$) for an extended period of time.

It is also known to combine the use of heat activation and a nutrient germinant to germinate spores in a two-step process in laboratory settings. The spores are first heat activated by incubating for a period of time (e.g. 30 minutes) at a temperature in the range of 65-75° C. (this specific temperature is species dependent). Then, the spores are transferred into a buffer solution that contains a nutrient germinant, such as L-alanine. It is also known to grow bacteria in a growth chamber located near a use site by feeding pelletized nutrient material (containing sugar, yeast extract, and other nutrients that are not direct spore germinants), bacteria starter, and water into a growth chamber at a controlled temperature range of 16-40° C., and more preferably between 29-32° C., for a growth period of around 24 hours as disclosed in U.S. Pat. No. 7,081,361.

There is a need for a rapid spore incubation and activation method that will allow generation of active *Bacillus* species in a single step at a point-of-use location where the bacteria will be distributed to a consumer/user, for example, in the way of a probiotic for use in human, animal or plant consumption or directly into a water treatment facility or a drain line. Accordingly, this invention describes a simple method for spore germination using a nutrient germinant concentrate simultaneously with heat incubation in a single step.

SUMMARY OF THE INVENTION

A nutrient-germinant composition according to one preferred embodiment of the invention comprises one or a combination of many L-amino acids, optionally D-glucose (which increases the binding affinity of L-amino acids for their cognate receptors in the spore coat), and a neutral buffer such as a phosphate buffer, and an industrial preservative, such as the commercially available Kathon/Lingaurd CG (which has active ingredients comprising methyl chloro isothiazolinone and methyl isothiazolinone). A nutrient-germinant composition according to another preferred embodiment of the invention comprises one or a combination of two or more L-amino acids, optionally D-glucose (which increases the binding affinity of L-amino acids for their cognate receptors in the spore coat), HEPES sodium salt (a biological buffer to provide the proper pH for spore germination), and an industrial preservative, such as a combination of propylparaben and methylparaben or other GRAS (Generally Regarded As Safe) preservatives. According to another preferred embodiment, the composition also comprises a source of potassium ions, such as potassium chloride or monopotassium phosphate or dipotassium phosphate. According to another preferred embodiment, the composition includes both D-glucose and D-fructose.

According to another preferred embodiment, the composition also comprises spores of one or more *Bacillus* species and includes a germination inhibitor, such as NaCl, industrial preservatives, or D-alanine, in combination with any of the previously described composition ingredients. The germination inhibitor prevents the spores from germinating prematurely in the nutrient-germinant composition. The germination inhibitor may include chemicals that prevent spore germination such as NaCl, industrial preservatives, or D-alanine. Alternatively, bacterial spores may be separately provided and added to a nutrient-germinant composition according to the invention at the point-of-use and incubation.

According to another preferred embodiment, a nutrient germinant composition according to the invention is in concentrated form and is diluted to 0.01% to 10% strength in water or another diluent at the point-of-use. The use of a concentrated formula reduces shipping, storage, and packaging costs and makes dosing of the composition at the point-of-use easier. Most preferably, the concentrated composition is in a liquid form, which is easier and faster to mix with diluent at the point-of-use, but solid forms such as pellets or bricks or powder may also be used. The inclusion of a general, industrial preservative in the composition aids in long-term storage and/or germination inhibition, which is particularly useful when the composition is in the preferred concentrated form.

In another preferred embodiment, the present invention comprises a method of germinating spores of *Bacillus* species using a nutrient germinant composition at an elevated temperature; preferably in a range of 35-60° C., more preferably in the range of 38-50° C., and most preferably in the range of 41° C. to 44° C. for a period of time (an incubation period). The incubation period preferably ranges from 2-60 minutes, depending on the application. Most preferably, a nutrient-germinant composition in concentrated form according to a preferred composition of the invention is used in the incubation methods of the invention, but other nutrient-germinant compositions may also be used. Preferably, the incubation method is carried out at or near the point-of-use—the site or near the site where the germinated spores will be used (such as near animal feeding, watering, or bedding sites) or consumed and further comprises dispensing the germinated spores to the point-of-use/consumption. Preferred methods according to the invention may be carried out in any incubation device that has a reservoir capable of holding a volume of spores, liquid (typically water), nutrient-germinant composition and that is capable of heating the mixture during an incubation period. Most preferably, the methods are carried out in a device that is also capable of mixing those ingredients, automatically shutting-off heating at the end of the incubation period, and automatically dispensing a probiotic or treatment solution comprising the spores to a point-of-use/consumption. Preferred methods may also be carried out as a batch process or as a continuous process. Any variety of spore forms, such as dried powder form, a liquid suspension, or a reconstituted aqueous mixture, may be used with the method of the invention.

The preferred embodiments of the invention have broad utility and application and will allow for rapid germination of spores of *Bacillus* species at a point-of-use. The preferred embodiments are particularly useful in preparing spores for use as a probiotic, for feeding to animals for example, and for providing bacteria to treat wastewater systems or provide drain maintenance.

BRIEF DESCRIPTION OF THE DRAWINGS

The invention is further described and explained in relation to the following drawings wherein.

DESCRIPTION OF THE PREFERRED EMBODIMENTS

Figure 1:
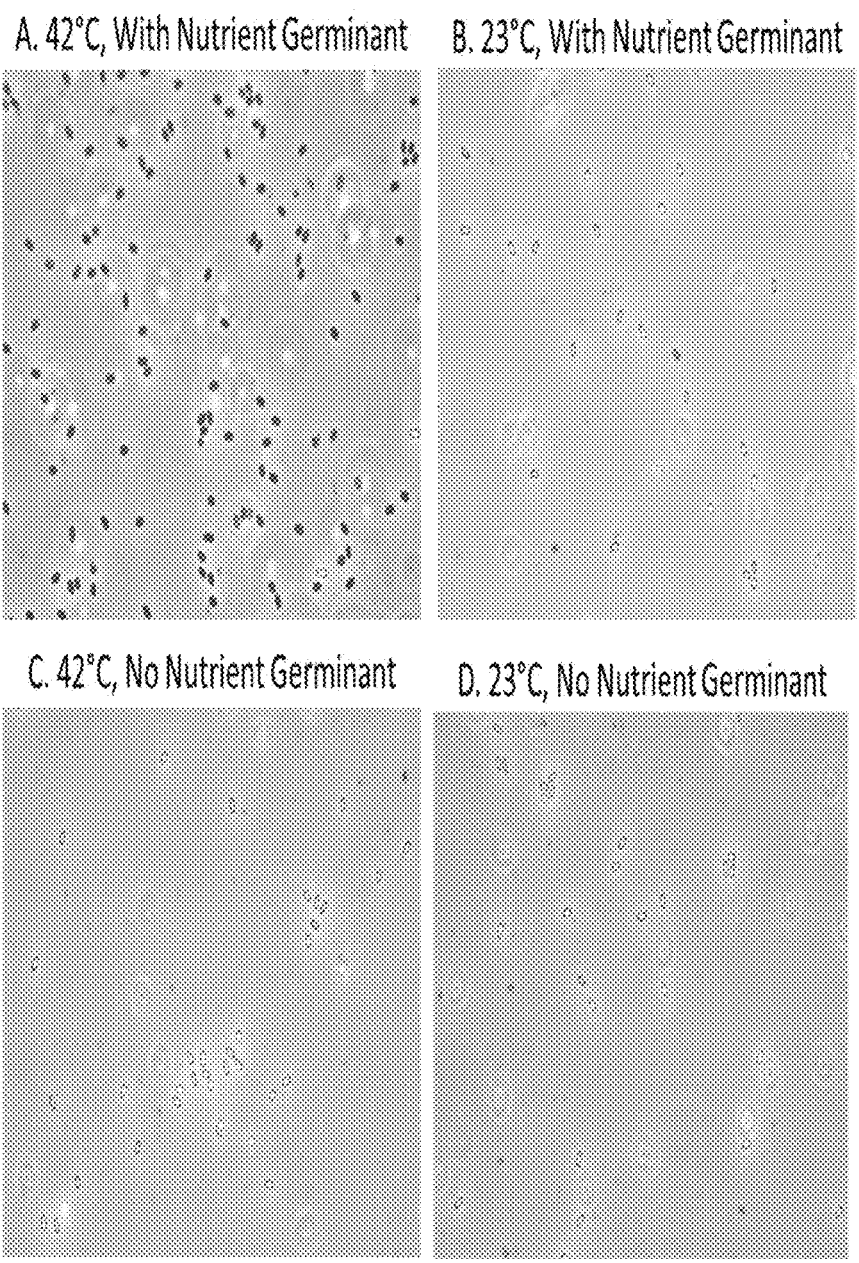
FIG. 1 shows photographs of bacteria slides using a composition and method according to a preferred embodiment of the invention compared to control slides.

A nutrient-germinant composition according to one preferred embodiment of the invention comprises one or more L-amino acids, D-glucose (which increases the binding affinity of L-amino acids for their cognate receptors in the spore coat and is optional), D-Fructose (optional, depending on bacteria species), a biological buffer to provide the proper pH for spore germination (such as HEPES sodium salt, a phosphate buffer, or a Tris buffer), an optional source of potassium ions (such as KCl), and an industrial preservative. In another preferred embodiment, the composition comprises both D-glucose and D-fructose. It is most preferred to include a source of potassium ions, such as KCl, when both D-glucose and D-fructose are used. The use of D-fructose, a combination of D-glucose and D-fructose, and a potassium ion source are dependent on the species of bacteria as will be understood by those of ordinary skill in the art. It is preferred to use a preservative that is pH compatible with the composition, which has a relatively neutral pH. According to another preferred embodiment, the composition also comprises spores of one or more *Bacillus* species and one or more germination inhibitors. Alternatively, spores may be separately added to the nutrient-germinant composition according to the invention at the point-of-use. According to another preferred embodiment, the composition is in a concentrated form, most preferably as a concentrated liquid, and is diluted at the point-of-use.

Preferred L-amino acids include L-alanine, L-asparagine, L-valine, and L-cysteine. In a further embodiment of the concentrate composition, L-amino acids can be provided as a hydrolysate of soy protein. When in a concentrated form, the composition preferably comprises a solution of one or more of the above mentioned L-amino acids in the weight range of 8.9-133.5 g/L, more preferably 13.2-111.25 g/L, and most preferably 17.8-89 g/L each; D-glucose (optional) and/or D-fructose (optional) in the weight range of 18-54 g/L, more preferably 27-45 g/L, and most preferably 30-40 g/L each; KCl (optional, as a source of potassium) in the weight range of 7.4-22.2 g/L, more preferably 11.1-18.5 g/L, and most preferably 14-16 g/L; monosodium phosphate in a weight range of 10-36 g/L, more preferably 15-30 g/L, and most preferably 20-24 g/L; disodium phosphate in a weight range of 30-90 g/L, more preferably 21.3-75 g/L, and most preferably 28.4-60 g/L; and an one or more industrial preservatives at a final (total) weight range of 0.8-3.3 g/L, more preferably 1.2-2.7 g/L, most preferably 1.6-2.2. In addition to or in place of the monosodium/disodium phosphate buffer, the composition may comprise Tris base in a weight range of 15-61 g/L, more preferably 24-43 g/L, and most preferably 27-33 g/L; or HEPES buffer in a weight range of 32.5 97.5 g/L, more preferably 48.75-81.25 g/L, and most preferably 60-70 g/L. Optionally, monopotassium phosphate may also be used as a source of potassium ions, preferably in a weight range of 13.6-40.8 g/L, more preferably 20.4-34 g/L, and most preferably 26-29 g/L. Optionally, dipotassium phosphate may also be used as a source of potassium ions, preferably in a weight range of 8.7-26.1 g/L, more preferably 13-21.75 g/L, and most preferably 16-19 g/L. The amounts of these ingredients are important aspects of the invention because higher concentrations would render some ingredients insoluble and lower concentrations would be ineffective at germinating spores.

Most preferably, a nutrient-germinant concentrate composition according to embodiments of the invention is in concentrated form and is diluted to a working solution in water or any other appropriate diluent, preferably at the point-of-use. The dilution is preferably in a range from 0.1-10% of the concentrate and the balance water, but other amounts may also be used. The use of a concentrated formula reduces shipping, storage, and packaging costs and makes dosing of the composition at the point-of-use easier. Most preferably, the concentrated composition is in a liquid form, which is easier and faster to mix with diluent at the point-of-use, but solid forms such as pellets or bricks or powder may also be used. The inclusion of a general, industrial preservative in the composition aids in long-term storage and/or germination inhibition, which is particularly useful when the composition is in the preferred concentrated form.

According to one preferred embodiment, the composition preferably comprises 10% to 90% by weight of one or more *Bacillus* spores. The preferred *Bacillus* spores include the following species: *Bacillus licheniformis, Bacillus subtilis, Bacillus amyloliquiefaciens, Bacillus polymyxa, Bacillus thuringiensis, Bacillus megaterium Bacillus coagulans, Bacillus lentus, Bacillus clausii, Bacillus circulans, Bacillus firmus, Bacillus lactis, Bacillus laterosporus, Bacillus laevolacticus, Bacillus polymyxa, Bacillus pumilus, Bacillus simplex,* and *Bacillus sphaericus.* Other *Bacillus* spore species may also be used as will be understood by those of ordinary skill in the art. Most preferably, the composition comprises 3 to 12 *Bacillus* species. Alternatively, these spores may be separately added to the nutrient-germinant composition at the point-of-use.

In another preferred embodiment, a nutrient-germinant composition for use as a probiotic comprises one or more *Bacillus* strains that are probiotic in nature in that they aid in the breakdown of nutrients in the digestive tract of the consumer. The strains preferably produce one or more of the following enzymes: proteases to hydrolyze proteins, amylases to hydrolyze starches and other carbohydrates, lipases to hydrolyze fats, glycosidases to assist in the hydrolysis of glycosidic bonds in complex sugars and to assist in degradation of cellulose, cellulases to degrade cellulose to glucose, esterase which is a lipase-like enzyme, and xylanases that degrade xylan, a polysaccharide found in plant cell walls. *Bacillius* strains that produce these enzymes are well known in the art. Alternatively, these *Bacillus* strains may also be separately added to the nutrient-germinant composition at the point-of-use.

In another embodiment, a nutrient-germinant composition for use as a wastewater treatment or a drain treatment comprises one or more *Bacillus* strains that produce enzymes that are beneficial in the digestion of organic matter typically found in wastewater and/or drains. The *Bacillus* strains preferably produce one or more of the following enzymes: proteases to hydrolyze plant and animal proteins, amylases to hydrolyze starches and other carbohydrates, lipases to hydrolyze vegetable and animal fats, oils, and grease, glycosidases to assist in the hydrolysis of glycosidic bonds in complex sugars and to assist in degradation of cellulose, cellulases to degrade cellulose to glucose, esterase which is a lipase-like enzyme, and xylanases. Other enzymes may be produced, as well. The particular *Bacillus* species selected for inclusion in a preferred composition according to the invention may be one that specifically produces enzymes targeted for the particular type of organic matter that is found in the wastewater and/or drain being treated. *Bacillius* strains that produce these enzymes or are targeted for particular types of waste treatment are well known in the art. Again, as another alternative, these *Bacillus* strains may also be separately added to the nutrient-germinant composition at the point-of-use.

When spores are included in the nutrient-germinant composition, the composition also comprises one or more germination inhibitors and/or preservatives. Preferred germination inhibitors or preservatives include NaCl, D-alanine, or preservatives. Specifically, the composition comprises a high concentration of NaCl in the range of 29-117 g/L, more preferably 43-88 g/L, most preferably 52-71 g/L, and/or one or more chemical preservatives (such as Linguard ICP or Kathon CG (which has active ingredients comprising methyl chloro isothiazolinone, around 1.15-1.18% and methyl isothiazolinone, around 0.35-0.4%)) at a final (total) concentration of 0.8-3.3 g/L, more preferably 1.2-2.7 g/L, most preferably 1.6-2.2 g/L, and/or D-alanine (a known competitive inhibitor of germination) in the range of 8-116 g/L, more preferably 26-89 g/L, most preferably 40-50 g/L. These germination inhibitors or preservatives maintain the spores in an inactive state and prevent premature germination of the spores prior to their dilution and activation at the point-of-use. The use of germination inhibitors is particularly preferred when the composition according to this embodiment is used with the preferred method of the invention, where germination occurs at the point-of-use. The nutrient-germinant composition according to the invention optionally comprises other standard ingredients including, but not limited to, other preservatives that ensure the shelf-life of the composition and surfactants that aid in the dispersal of active ingredients, that are typically included in spore compositions or in industrial treatment products.

According to one preferred embodiment, a method of germinating spores at a point-of-use according to the invention comprises providing a composition comprising spores and nutrients (preferably a composition according to the invention, but the spores and nutrients may also be in separate compositions/separately added components) and heating the composition to an elevated temperature or range of temperatures and maintaining the composition at that temperature or within that range for a period of time (incubation period) to allow germination at a point-of-use location near a point-of-consumption. Heating during the incubation period takes place in the presence of the nutrient-germination composition in a single step. The method also preferably comprises the step of dispensing the germinated spores to an animal (through feed or water), animal bedding, plants, ponds, humans, wastewater system, or drain. Preferably, the spore composition is heated to a temperature in a range of 35-55° C., more preferably in the range of 38-50° C., and most preferably in the range of 41° C. to 44° C. The incubation period can vary depending on the end-use application. For a probiotic application, it is preferred that the incubation period lasts no longer than 10 minutes. Most preferably, in a probiotic application, the incubation period is between 2-5 minutes. In this way, spores are released to the animal before the spores have fully germinated and stand a better chance of surviving through to the animal's intestinal tract where they are most beneficial. On the other hand, a wastewater application may require a longer incubation period ranging between 20-60 minutes to ensure that fully germinated spores are delivered to the wastewater being treated. Most preferably, the incubation period is between 20-30 minutes for wastewater treatment. Regardless of application, the incubation may be in an air incubator, a water incubator, or any other chamber that provides even, constant heat at the given temperature range.

Various compositions according to preferred embodiments of the invention were tested according to preferred methods of the invention. The compositions, methods, and results are described below.

EXAMPLE 1

To germinate spores, FreeFlow LF-88 Probiotic (spore liquid formula commercially available from NCH Corporation) was added to 1 mL of tap water at a final concentration of approx. $1 \times 10^9$ CFU/mL, where CFU stands for colony forming unit. A nutrient germinant concentrate composition according to a preferred embodiment of the invention comprising L-alanine (89 g/L), monosodium phosphate (20 g/L), disodium phosphate (60 g/L), and Linguard CP (1.6 g/L total) was added to the water and bacteria mixture to provide a 4% final concentration of nutrient-germinant composition by total weight of the mixture. For comparison, negative control reactions were prepared with the same amount of FreeFlow LF-88 Probiotic and water, but without adding the nutrient germinant concentrate composition. Both mixtures (germinant and negative control without the nutrient-germinant composition) were blended and incubated for 60 minutes in a pre-incubated heat block set to 42° C. or at ambient room temperature (around 23° C.).

Spores from each reaction were observed using phase contrast microscopy. Slides were prepared using standard procedures. Spores were viewed on an Olympus BX41 microscope (100× oil emersion objective) and imaged using an Olympus UC30 camera controlled by the cellSens Dimension software package.

Images were taken and germinated spores were counted as a percentage of the total spores in the field. A total of 10 representative images were analyzed for each condition (test mixture). Germinated spores lose their refractivity due to the influx of water and are phase-dark while non-germinated spores are phase-bright.

FIG. 1 shows representative images from these tests. Image A represents spores that had been germinated using a nutrient-germinant composition and heated during the incubation period at 42° C. according to a preferred composition and preferred method of the invention. The darker spots show germinated spores, the lighter spots show non-germinated spores. Image B represents spores that had been germinated using a nutrient-germinant composition according to a preferred embodiment of the invention, but were incubated at ambient temperature (23° C.). Images C-D represent control spores that had not been treated with a nutrient germinant composition according to the invention, one having been incubated at 42° C. and one incubated at ambient temperature (23° C.).

As can be seen in FIG. 1, the "A" image shows significantly more germinated spores (dark spots) than the other images. Spores incubated with a nutrient-germinant composition according to a preferred embodiment invention in combination with a germination method according to a preferred embodiment of the invention show an apparent germination efficiency of 96.8% (Example 1, FIG. 1A). Control spores that had been incubated with a nutrient-germinant composition according to a preferred embodiment of the invention, but without using a germination method according to a preferred embodiment of the invention showed an apparent germination efficiency of 2.3% (Example 1, FIG. 1B). Similarly, spores that had not been incubated with a nutrient-germinant composition according to the invention showed an apparent activation efficiency of 1.2% and 2.6% at 42° C. and 23° C., respectively (Example 1, FIGS. 1C and 1D). Germinated spores in the samples not treated by preferred embodiments of the present method represent the small percentage of spores already germinated in the FreeFlow LF-88 Probiotic solution. This example demonstrates that spore germination is significantly increased when a nutrient-germinant composition and incubation method according to preferred embodiments of the invention are used together.

EXAMPLE 2

Another set of incubation tests were run using the same test mixture/incubation method (using the same nutrient-germinant composition and heated incubation, "Treated Spores, 42° C.") and control mixture/incubation method (no nutrient-germinant composition and no heat, "Non-treated Spores, 23° C.") as described above in Example 1 were repeated, but different tests were run to compare the efficacy of the test mixture according to preferred embodiments of the invention as compared to the control mixture. Additionally, two other mixtures were tested—one in which the nutrient-germinant composition of Example 1 was used but without heat ("Treated Spores, 23° C.") and one in which no nutrient-germinant was used but the spores were heated ("Non-Treated Spores, 42° C."). Briefly, spores were incubated at 42° C. or 23° C. for 1 hour with or without treatment with a preferred nutrient-germinant composition. After incubation, the spores from 1 mL of each reaction were pelleted at 14K RPM for 3 min at 23° C. and resuspended in 1 mL of Butterfield's buffer. Approx. $6 \times 10^5$ CFUs (0.02 mL) were added to 0.980 mL of Davis minimal media (containing 3% glucose as a carbon source and trace elements) with an excess of D-alanine. D-alanine is a potent inhibitor of L-amino acid-mediated germination.

Approx. $1.2 \times 10^5$ CFUs were added to each of four wells of a PreSens OxoPlate. PreSens OxoPlates use optical oxygen sensors to fluorescently measure the oxygen content of the sample using two filter pairs (excitation: 540 nm, emission: 650 nm and excitation: 540, emission: 590 nm). Controls were performed as described by the manufacturer and measurements were taken on a BioTek 800FLx fluorescence plate reader. Time points were taken every 10 minutes for 24 hours at 37° C. with continual shaking and data was processed to determine the partial pressure of oxygen ($pO_2$) using the following formula:

$$pO_2 = 100 * [(K_0/IR) - 1(K_0/K_{100}) - 1]$$

Spores that have germinated and continue to divide and grow as vegetative cells consume oxygen as part of their metabolic growth. Oxygen consumption is represented by a drop in $pO_2$. Presumably, the growth that is observed is due to the outgrowth and vegetative growth of spores germinated by the present invention. The $pO_2$ levels for these tests are shown in FIG. 2.

Figure 2:
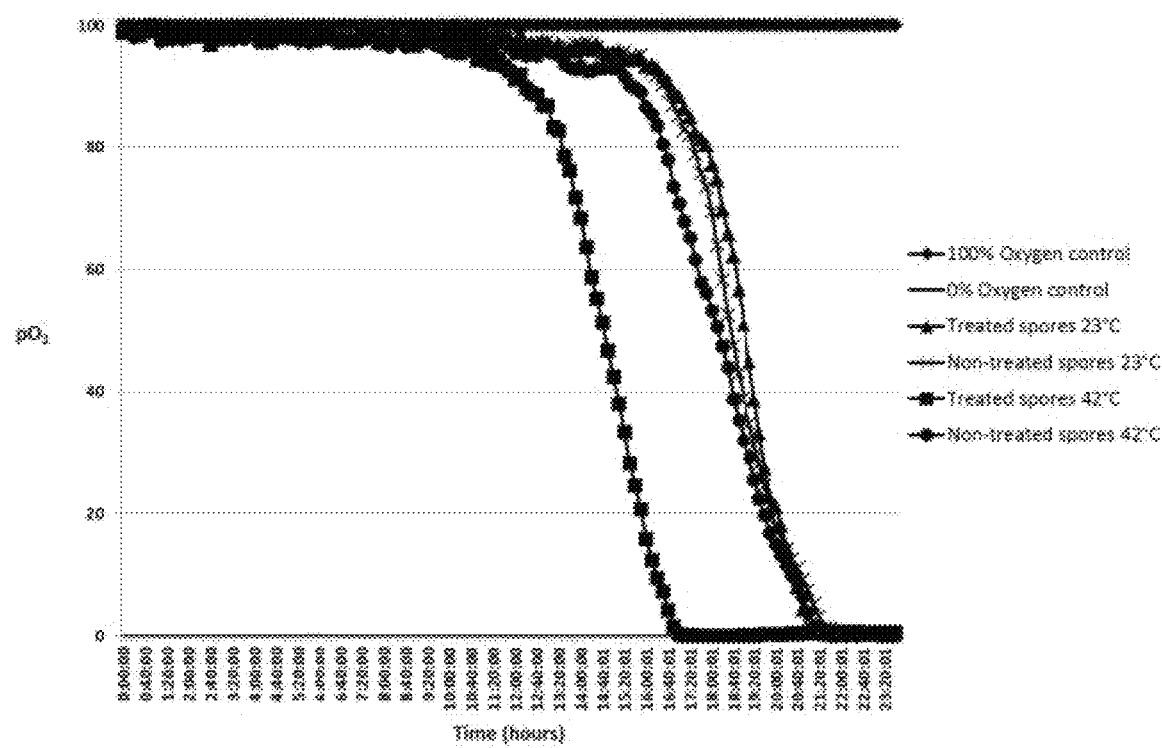
FIG. 2 is a graph showing $pO_2$ test data to demonstrate germination levels using a composition and method according to a preferred embodiment of the invention compared to control tests.

As shown in FIG. 2, incubation with the test mixture and method according to preferred embodiments of the invention (Treated spores 42° C., using both the nutrient-germinant composition and heating) resulted in spores that began vegetative growth 4 hours faster than the control spore mixtures that had not been treated or heated according to preferred embodiments of the invention or had been either treated with a nutrient-germinant composition or heated, but not both together. The growth seen in the control experiments presumably represents the approx. 2% of germinated spores present in FreeFlow LF-88 Probiotic (see EXAMPLE 1). This example further indicates that spore germination is significantly increased when a nutrient-germinant composition and incubation method according to preferred embodiments of the invention are used.

EXAMPLE 3

Another set of incubation tests were run using a similar test and control mixture and incubation method as described above in Example 1. Briefly, LF-88 was added to 10 mLs of distilled water at a final concentration of approx. $10^8$ CFU/mL. Samples were incubated at various temperatures to show the efficacy of the test method according to preferred embodiments of the invention as compared to the control mixture. Reactions were prepared with the nutrient-germinant composition described in Example 1 ("Treated spores" in FIG. 3) and incubated at 23° C. (ambient temperature, no heating), 32° C., 42° C., or 60° C. A control reaction was incubated at ambient room temperature with no nutrient-germinant composition. After one hour of incubation, 1 mL of each reaction was pelleted at 14K RPM for 3 min at 23° C. and resuspended in Butterfield's buffer. Approx $6\times10^5$ CFUs (0.02 mL) were added to 0.980 mL of Davis minimal media (containing 3% glucose as a carbon source and trace elements) with an excess of D-alanine.

Approx. $1.2\times10^5$ CFUs were added to each of four wells of a PreSens OxoPlate. Controls were performed as described by the manufacturer and measurements were taken on a BioTek 800FLx fluorescence plate reader using two filter pairs (excitation: 540 nm, emission: 650 nm and excitation: 540, emission: 590 nm). Time points were taken every 10 minutes for 24 hours at 37° C. with continual shaking and data was processed to determine the partial pressure of oxygen ($pO_2$). The $pO_2$ levels for these tests are shown in FIG. 3.

Figure 3:
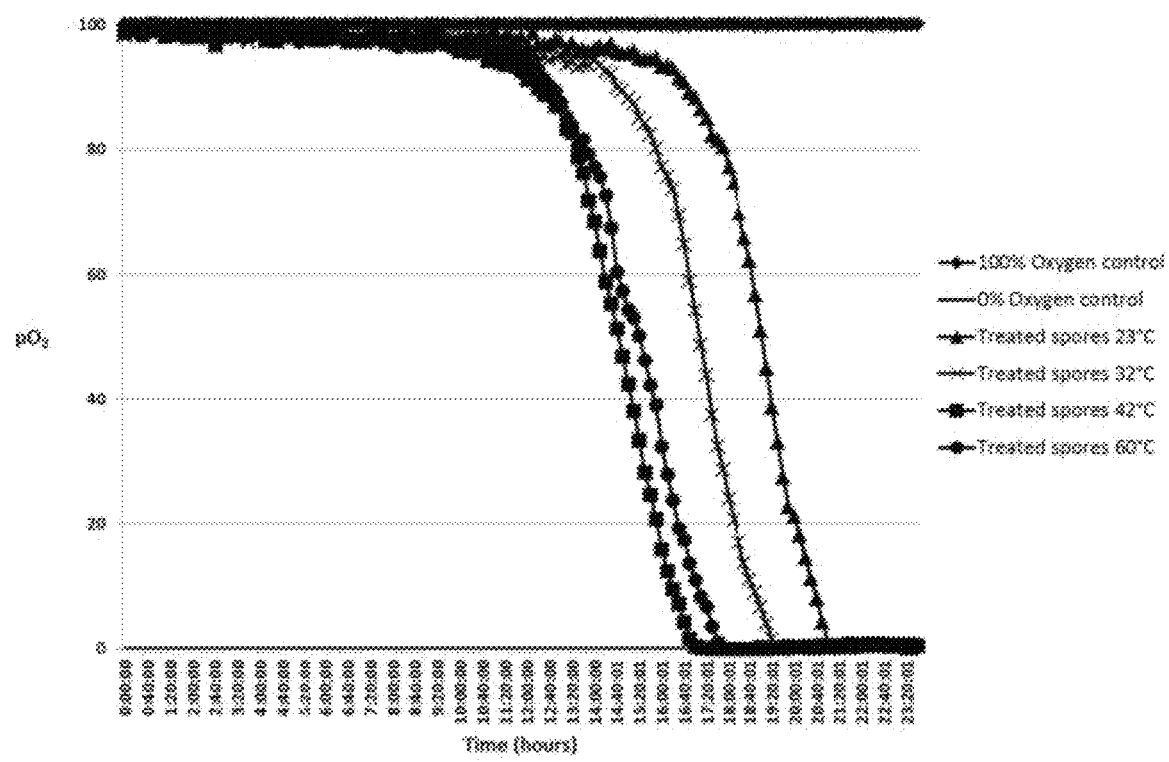
FIG. 3 is a graph showing $pO_2$ test data to demonstrate germination levels using a composition and varied methods according to preferred embodiments of the invention compared to control tests.

As shown in FIG. 3, incubation using a nutrient-germinant composition and heating according to preferred embodiments of the invention resulted in spores that began vegetative growth hours before the control. Spores treated with the nutrient-germinant composition but not heated are comparable to the control mixture. Spores treated with the nutrient-germinant composition that were incubated at a temperature below the preferred range of range of 35-55° C. according to one embodiment of the invention (represented by the "Treated spores 32° C." curve) begin vegetative growth faster than control experiments, but not as fast as spores treated at elevated temperatures within the preferred ranges according to the invention. Spores treated with a nutrient-germinant composition and incubated at a temperature within the most preferred range of 41° C. to 44° C. according to an embodiment of the invention showed the best results, being the first to begin vegetative growth and beginning growth 4 hours faster than the control. As seen in previous examples, growth seen in the no-treatment control experiment presumably represents the approx. 2% of germinated spores present in FreeFlow LF-88 Probiotic (see EXAMPLE 1). This example further indicates that spore germination is significantly increased when a nutrient-germinant composition and incubation method according to preferred embodiments of the invention are used.

Those of ordinary skill in the art will also appreciate upon reading this specification and the description of preferred embodiments herein that modifications and alterations to the device may be made within the scope of the invention and it is intended that the scope of the invention disclosed herein be limited only by the broadest interpretation of the appended claims to which the inventors are legally entitled.

We claim:
1. A method of germinating bacterial spores at a point of use comprising the following steps:
   providing a nutrient-germinant composition and spores of a bacteria species, if not included in the nutrient-germinant composition;
   heating the nutrient-germinant composition and spores to a temperature in a range of around 35° C. to 60° C. at or near a point-of-use;
   maintaining the temperature for an incubation period of around 2 to 60 minutes to form a germinated spore solution;
   dispensing the germinated spore solution to the point-of-use and wherein the point of use comprises animal feed, animal water, animal bedding, a plant, a pond, a wastewater system, or a drain and
   wherein the nutrient-germinant composition comprises: (1) one or more L-amino acids; (2) one or more buffers comprising a phosphate buffer, HEPES, Tris base, or a combination thereof; (3) an industrial preservative; and (4) optionally a source of potassium ions.

2. The method of claim 1 wherein the nutrient-germinant composition is in a concentrated liquid form and further comprising:
   adding a diluent to the nutrient-germinant composition;
   mixing the diluted nutrient-germinant composition and bacterial spores during the incubation period; and
   wherein the concentration of the diluted nutrient-germinant composition is around 0.1% to 10%.

3. The method of claim 1 wherein the temperature range is around 41° C. to 44° C.

4. The method of claim 1 wherein the L-amino acid is L-alanine, L-asparagine, L-valine, L-cysteine, a hydrolysate of soy protein, or a combination thereof.

5. The method of claim 1 wherein the nutrient-germinant composition is in a concentrated liquid form comprising around 17.8 g/L to 89 g/L total of one or more L-amino acids, the method further comprising:
   adding a diluent to the nutrient-germinant composition;
   mixing the diluted nutrient-germinant composition and bacterial spores during the incubation period; and
   wherein the concentration of the diluted nutrient-germinant composition is 0.01% to 10% of the concentrated nutrient-germinant composition.

6. The method of claim 5 wherein the nutrient-germinant composition further comprises spores of a *Bacillus* species and a germination inhibitor.

7. The method of claim 6 wherein the germination inhibitor or preservative comprises sodium chloride, D-alanine, or a combination thereof.

8. The method of claim 7 wherein the concentrated nutrient-germinant composition comprises around 29 g/L to 117 g/L sodium chloride.

9. The method of claim 7 wherein the concentrated nutrient-germinant composition comprises around 8 g/L to 116 g/L D-alanine.

10. The method of claim 6 wherein the *Bacillus* species is *Bacillus licheniformis, Bacillus subtilis, Bacillus amyloliquiefaciens, Bacillus polymyxa, Bacillus thuringiensis, Bacillus megaterium, Bacillus coagulans, Bacillus lentus, Bacillus clausii, Bacillus circulans, Bacillus firmus, Bacillus lactis, Bacillus laterosporus, Bacillus laevolacticus, Bacillus pumilus, Bacillus simplex*, and *Bacillus sphaericus*, or a combination thereof.

11. The method of claim 6 wherein the point of use comprises animal feed or animal water or both and wherein the *Bacillus* species are capable of producing enzymes that aid in the breakdown of organic matter in the digestive tract of a consuming animal.

12. The method of claim 11 wherein the wherein the enzymes comprise amylase, protease, lipase, esterase, urease, cellulase, xylanase, or a combination thereof.

13. The method of claim 1 wherein the nutrient-germinant composition is a concentrated liquid comprising:
around 8.9-133.5 g/L of one or more L-amino acids;
around 0.8-3.3 g/L total of the one or more industrial preservatives;
around 10-36 g/L monosodium phosphate, or around 30-90 g/L disodium phosphate, or around 15-61 g/L Tris base, or around 32.5-97.5 g/L HEPES, or a combination thereof; and
optionally around 18-54 g/L of D-glucose, D-fructose, or a combination thereof.

14. The method of claim 13 further comprising:
adding a diluent to the nutrient-germinant composition; and
mixing the diluted nutrient-germinant composition and bacteria spores during the incubation period.

15. The method of claim 14 wherein the concentration of the diluted nutrient-germinant composition is around 4% to 10%.

16. The method of claim 1 wherein the nutrient-germinant composition is a concentrated liquid comprising:
around 13.2-111.25 g/L of L-alanine;
around 0.8-3.3 g/L total of propylparaben or methylparaben or both;
one or more buffers comprising a phosphate buffer, HEPES, Tris base, or a combination thereof;
a source of potassium ions;
optionally spores of one or more *Bacillus* species; and
wherein if spores are included, the concentrated nutrient-germinant composition further comprises around 29 g/L to 117 g/L sodium chloride or around 8 g/L to 116 g/L D-alanine or both.

17. The method of claim 16 further comprising:
adding a diluent to the nutrient-germinant composition prior to or during the heating step; and
wherein the concentration of the diluted nutrient-germinant composition is around 4% of the concentrated liquid.

18. The method of claim 1 wherein the nutrient-germinant composition does not include fructose or glucose.

19. The method of claim 13 wherein the nutrient-germinant composition does not include fructose or glucose.

20. The method of claim 16 wherein the nutrient-germinant composition does not include fructose or glucose.

21. The method of claim 1 wherein the incubation period is 2 to 5 minutes.

22. The method of claim 13 wherein the incubation period is 2 to 5 minutes.

23. The method of claim 16 wherein the incubation period is 2 to 5 minutes.

24. The method of claim 1 wherein the industrial preservative comprises propylparaben, methylparaben, methyl chloro isothiazolinone, methyl isothiazolinone or a combination thereof and wherein the nutrient-germinant composition does not include fructose or glucose.

25. The method of claim 1 wherein the spores are not heat activated prior to heating with the nutrient-germinant composition.

26. The method of 18 wherein the spores are not heat activated prior to heating with the nutrient-germinant composition.

27. The method of claim 1 wherein the spores are *Bacillus subtilis*, or *Bacillus licheniformis*, or both.

28. A method of germinating bacterial spores at a point of use comprising the following steps:
providing a nutrient-germinant composition and spores of a bacteria species, if not included in the nutrient-germinant composition;
heating the nutrient-germinant composition and spores to a temperature in a range of 38° C. to 60° C.;
maintaining the temperature in the range for an incubation period of around 2 to 60 minutes to form a germinated spore solution; and
dispensing the germinated spore solution to the point-of-use and wherein the point of use comprises animal feed, animal water, animal bedding, a plant, a pond, a wastewater system, or a drain; and
wherein the spores are not heat activated prior to heating with the nutrient-germinant composition.

29. The method of claim 27 wherein the nutrient-germinant composition wherein the nutrient-germinant composition comprises: (1) one or more L-amino acids; (2) one or more buffers comprising a phosphate buffer, HEPES, Tris base, or a combination thereof; (3) an industrial preservative; and (4) an optional source of potassium ions.

30. The method of claim 29 wherein the spores are *Bacillus subtilis*, or *Bacillus licheniformis*, or both.

31. The method of claim 29 wherein the temperature range is 41° C. to 44° C.

32. The method of claim 1 further comprising dispensing the germinated spore solution to the point-of-use and wherein the point of use comprises a wastewater system or a drain.

33. The method of claim 1 wherein the industrial preservative meets GRAS standards and the nutrient germinant composition comprises a source of potassium ions.

34. The method of claim 1 wherein the temperature is in a range of 44° C. to 60° C.

35. The method of claim 1 wherein the temperature is in a range of 38° C. to 50° C.

36. The method of claim 1 wherein the temperature is in a range of 38° C. to 60° C.

37. The method of claim 1 wherein the temperature range is 42° C. to 44° C.

38. The method of claim 2 wherein the concentrated nutrient-germinant composition comprises around 17.8 g/L to 89 g/L total of one or more L-amino acids and wherein the concentration of the diluted nutrient-germinant composition is around 0.1% to 10% of the concentrated nutrient-germinant composition.

39. The method of claim 1 wherein the temperature is 38° C.

40. The method of claim 1 wherein the temperature is 39° C.

41. The method of claim 1 wherein the temperature is 40° C.

42. The method of claim 1 wherein the temperature is 41° C.

43. The method of claim 1 wherein the temperature is 42° C.

44. The method of claim 1 wherein the temperature is 43° C.

45. The method of claim 1 wherein the temperature is 44° C.

46. The method of claim 1 wherein the temperature is 45° C.

47. The method of claim 1 wherein the temperature is 46° C.

48. The method of claim 1 wherein the temperature is 47° C.

49. The method of claim 1 wherein the temperature is 48° C.

50. The method of claim 1 wherein the temperature is 49° C.

51. The method of claim 1 wherein the temperature is 50° C.

52. The method of claim 1 wherein the temperature is 51° C.

53. The method of claim 1 wherein the temperature is 52° C.

54. The method of claim 1 wherein the temperature is 53° C.

55. The method of claim 1 wherein the temperature is 54° C.

56. The method of claim 1 wherein the temperature is 55° C.

57. The method of claim 1 wherein the temperature is 56° C.

58. The method of claim 1 wherein the temperature is 57° C.

59. The method of claim 1 wherein the temperature is 58° C.

60. The method of claim 1 wherein the temperature is 59° C.

61. The method of claim 1 wherein the temperature is 60° C.

62. The method of claim 1 wherein the nutrient-germinant composition is in a concentrated liquid form and further comprising:
    adding a diluent to the nutrient-germinant composition;
    mixing the diluted nutrient-germinant composition and bacterial spores during the incubation period; and
    wherein the concentration of the diluted nutrient-germinant composition is 4% to 10%.

63. The method of claim 1 wherein the one or more phosphate buffers comprises around 10-36 g/L monosodium phosphate, or around 21.3-75 g/L disodium phosphate, or around 15-61 g/L Tris base, or around 32.5-97.5 g/L HEPES, or a combination thereof.

\* \* \* \* \*